(12) United States Patent
Dübal et al.

(10) Patent No.: US 6,482,479 B1
(45) Date of Patent: Nov. 19, 2002

(54) ACTIVE MATRIX DISPLAYS HAVING HIGH CONTRAST VALUES

(75) Inventors: Hans-Rolf Dübal, Eltville (DE); Toshiaki Nonaka, Kakegawa (JP); Rainer Wingen, Hattersheim (DE)

(73) Assignee: Clariant International Ltd., Muttenz (CH)

( * ) Notice: Subject to any disclaimer, the term of this patent is extended or adjusted under 35 U.S.C. 154(b) by 120 days.

(21) Appl. No.: 09/626,217

(22) Filed: Jul. 26, 2000

(30) Foreign Application Priority Data

Jul. 28, 1999 (DE) .......................................... 199 34 799

(51) Int. Cl.$^7$ .................. C09K 19/02; C09K 19/34; C09K 19/12; C09K 19/20; C09K 19/42; G02F 1/13
(52) U.S. Cl. .............. 428/1.1; 252/299.01; 252/299.61; 252/299.64; 252/299.65; 252/299.67; 349/172
(58) Field of Search ........................ 252/299.01, 299.61, 252/299.64, 299.65, 299.67; 428/1.1; 349/172

(56) References Cited

U.S. PATENT DOCUMENTS 4,367,924 A    1/1983   Clark et al.

FOREIGN PATENT DOCUMENTS

| DE | 19922723 | * 11/2000 |
| EP | 0 032 362 | 7/1981 |

\* cited by examiner

*Primary Examiner*—Shean C. Wu
(74) *Attorney, Agent, or Firm*—Frommer Lawrence & Haug LLP

(57) ABSTRACT

An active matrix display comprises a chiral smectic liquid crystal mixture which has the phase sequence I—N*—SmC*, a spontaneous polarization in the operating temperature range of <40 nC/cm$^2$ and a pitch of >10 μm at at least one temperature in the nematic or cholesteric phase and comprises at least one compound each from at least two of the substance classes (A), (B) and (C) and one or more compounds from substance class (D):

Figure 1:
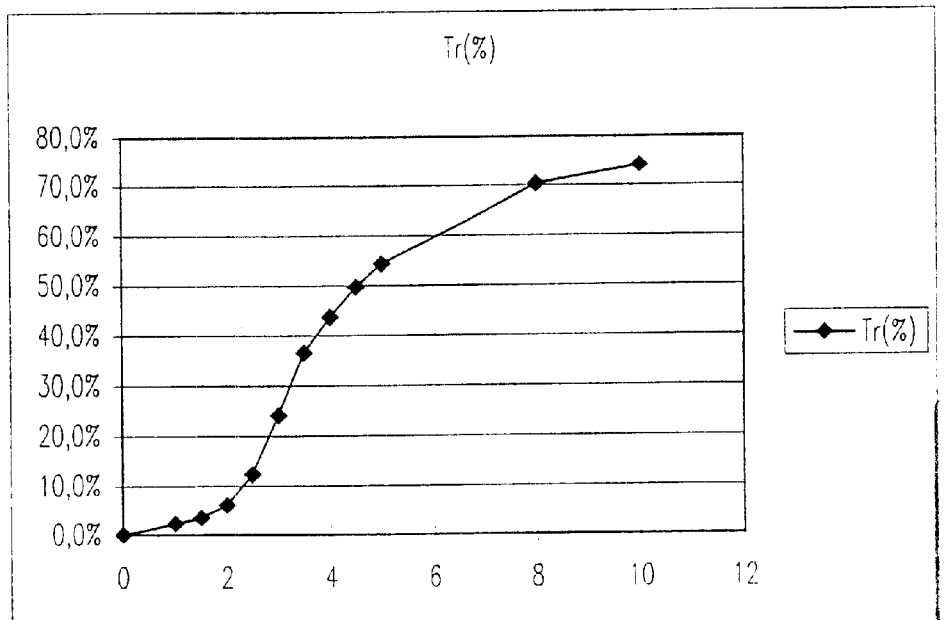

(A): compounds comprising two rings which are directly linked to one another and are selected from phenylene-1,4-diyl, pyrimidine-2,5-diyl, pyridine-2,5-diyl and pyridazine-2,5-diyl with the proviso that at least one of these rings is a nitrogen heterocycle;

(B): compounds comprising three rings selected from phenylene-1,4-diyl, two of the rings being directly linked to one another and the third ring being linked to one of the other two rings via an —OC(=O)— or —C(=O)—group, with the proviso that at least one of the three rings is fluorophenylene-1,4-diyl or ortho-difluorophenylene-1,4-diyl;

(C): compounds comprising three rings which are directly linked to one another and are selected from phenylene-1,4-diyl, pyrimidine-2,5-diyl, pyridine-2,5-diyl and pyridazine-2,5-diyl with the proviso that at least one of these rings is a nitrogen heterocycle;

(D): compounds comprising mesogenic groups suitable as components of liquid crystal mixtures.

7 Claims, 5 Drawing Sheets

ACTIVE MATRIX DISPLAYS HAVING HIGH CONTRAST VALUES

BACKGROUND OF THE INVENTION

Replacement of the cathode ray tube with a flat panel screen requires a display technology which simultaneously makes it possible to achieve a high resolution, i.e. more than 1000 lines, a high brightness (>200 cd/m$^2$), a high contrast (>100:1), a high frame rate (>60 Hz), an adequate color representation (>16 million), a large image format (>40 cm), a low power consumption and a wide viewing angle, at low production costs. At present, there is no technology which fully satisfies all these features simultaneously.

Many manufacturers have developed screens which are based on nematic liquid crystals and have been used in recent years in the field of notebook PCs, Personal Digital Assistants, desktop monitors etc. Use is made here of the technologies STN (supertwisted nematics), AM-TN (active matrix-twisted nematics) AM-IPS (active matrix-in plane switching) and AM-MVA (active matrix-multidomain vertically aligned), which are described in the relevant literature (see, for example, T. Tsukuda, TFT/LCD: Liquid Crystal Displays Addressed by Thin-Film Transistors, Gordon and Breach, 1996, ISBN 2-919875-01-9, and the references cited therein; SID Symposium 1997, ISSN-0097-966X, and the references cited therein). Furthermore, mention should be made of the technologies PDP (plasma display panel), PALC (plasma addressed liquid crystal), ELD (electroluminescent display), FED (field emission display) etc., which are also explained in the above-cited SID report.

Clark and Lagerwall (U.S. Pat. No. 4,367,924) have been able to show that the use of ferroelectric liquid crystals (FLCs) in very thin cells results in opto-electrical switching or display elements which have response times which are faster by a factor of up to 1000 compared with conventional TN ("twisted nematic") cells (see, for example, EP-A 0 032 362). Owing to this and other favorable properties, for example the possibility of bistable switching and the fact that the contrast is virtually independent of the viewing angle, FLCs are basically suitable for areas of application such as computer displays and TV sets, as shown by a monitor marketed in Japan by Canon since May 1995.

The use of FLCs in electro-optical or fully optical components requires either compounds which form tilted or orthogonal smectic phases and are themselves optically active, or the induction of ferroelectric smectic phases by doping corn-pounds which, although forming such smectic phases, are not themselves optically active, with optically active compounds. The desired phase should be stable over the broadest possible temperature range to ensure that the display has a broad operating range. In particular, the contrast obtainable should be as high as possible over the entire operating range.

In so-called active matrix technology (AMLCD), a non-structured substrate is usually combined with an active matrix substrate. An electrically non-linear element, for example a thin-film transistor, is integrated into each pixel of the active matrix substrate. The nonlinear elements can also be diodes, metal-insulator-metal and similar elements, which are advantageously produced by thin-film processes and are described in the relevant literature (see, for example, T. Tsukuda, TTT/LCD: Liquid Crystal Displays Addressed by Thin-Film Transistors, Gordon and Breach, 1996, ISBN 2-919875-01-9, and the references cited therein).

Active matrix LCDs are usually operated with nematic liquid crystals in TN (twisted nematics), ECB (electrically controlled birefringence), VA (vertically aligned) or IPS (in-plane switching) mode. In each case, the active matrix generates an electric field of individual strength on each pixel, producing a change in alignment and thus a change in birefringence, which is in turn visible in polarized light. A severe disadvantage of this process is the poor video capability, i.e. excessively slow response times, of nematic liquid crystals.

For this and other reasons, liquid crystal displays based on a combination of ferroelectric liquid crystal materials and active matrix elements have been proposed, for example in WO 97/12355, Ferroelectrics 1996, 179, 141–152, or W. J. A. M. Hartmann (IEEE Trans. Electron. Devices 1989, 36 (9;Pt. 1), 1895–9, and dissertation, Eindhoven, The Netherlands, 1990).

While Hartmann utilizes the charge-controlled bistability to display a virtually continuous gray scale, Nito et al. have suggested a monostable FLC geometry (Journal of the SID, 1/2, 1993, pages 163–169) in which the FLC material is aligned by means of relatively high voltages such that only a single stable position results from which a number of intermediate states are generated when an electric field is applied via a thin-film transistor. These intermediate states correspond to a number of different brightness values (gray shades) when the cell geometry is matched between crossed polarizers.

Figure 8:
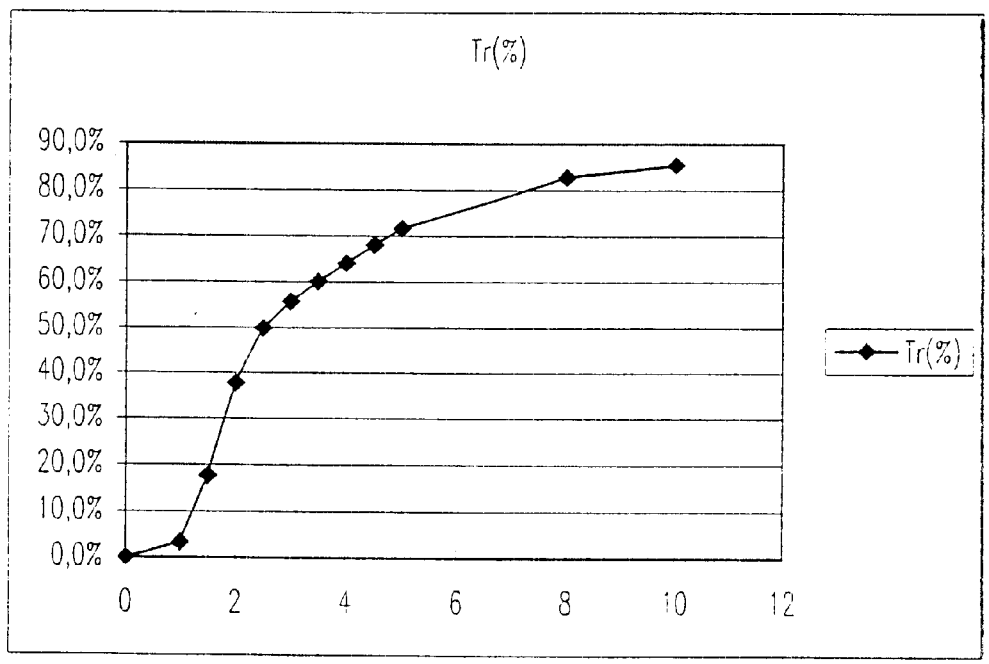

The disdavantage of the paper by Nito et al. is the occurrence of a streaky texture which limits contrast and brightness of this cell (see FIG. 8 of the abovementioned citation). Furthermore, this method produces switching only in an angle range of up to a maximum of once the tilt angle, which is about 22° in the case of the material used by Nito et al. (cf. p. 165, FIG. 6) and thus produces a maximum transmission of only 50% of the transmission of two parallel polarizers. Terada et al. have suggested a monostable FLC configuration (Applied Physics Conference, Mar. 28, 1999, Tokyo, Japan; Abstract No. 28p-V-8). However, these displays are not yet suitable for practical use over a relatively large temperature range.

OBJECTS AND SUMMARY OF THE INVENTION

The object of the present invention is to provide an active matrix liquid crystal display comprising a chiral smectic liquid crystal mixture where the liquid crystal mixture makes it possible to achieve a very high maximum transmission and a very high contrast and a constant threshold voltage over a broad temperature range.

In particular, a ferroelectric active matrix liquid crystal display comprising a ferrolelectric liquid crystal mixture is to be provided where the liquid crystal mixture assumes a monostable position, but without forming a streaky texture, is temperature-stable and makes it possible to achieve a very high maximum transmission and a very high contrast and a constant threshold voltage over a broad temperature range.

This object is achieved according to the invention by a chiral smectic active matrix display comprising a liquid crystal layer having the phase sequence I—N*—Sc*, a tilt angle which is virtually constant over a broad temperature range and a virtually constant deviation of the monostable position (i.e. the position in which the transmission of an FLC display arranged between two crossed polarizers is at a mininum) from the rubbing direction. The invention accordingly provides an active matrix display comprising a chiral smectic liquid crystal mixture where the liquid crystal mixture is characterized by the phase sequence I—N*—

SmC*, a spontaneous polarization in the operating temperature range of <40 nC/cm² and a pitch of >10 µm at at least one temperature in the nematic or cholesteric phase and comprises at least one compound each from at least two of the substance classes (A), (B) and (C) and from 0.1 to 50% by weight, based on the liquid crystal mixture, of one or more compounds from substance class (D)

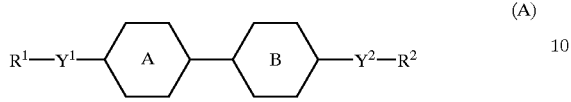
(A)

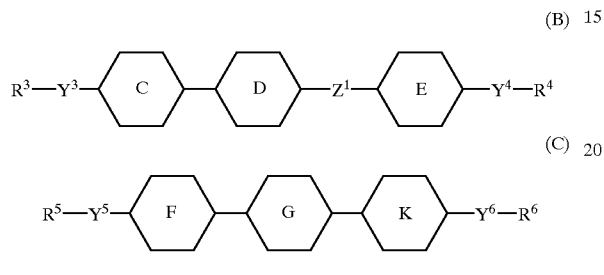
(B)

(C)

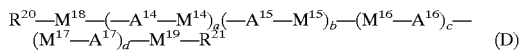

$$R^{20}-M^{18}-(-A^{14}-M^{14})_g(-A^{15}-M^{15})_b-(M^{16}-A^{16})_c-\\(M^{17}-A^{17})_d-M^{19}-R^{21}$$ (D)

where:
$R^1$, $R^2$, $R^3$, $R^4$, $R^5$, $R^6$ are each, independently of one another, hydrogen or a straight-chain or branched alkyl or alkenyl radical (with or without asymmetric carbon atoms) having 2 to 18 carbon atoms, where one or two nonterminal, nonadjacent —CH$_2$— groups may be replaced by —O— and/or one —CH$_2$— group may be replaced by —C≡C— or —Si(CH$_3$)$_2$— and one or more H atoms may be replaced by F with the provisos that heteroatoms cannot be adjacent and that in each case only one of $R^1$, $R^2$ or $R^3$, $R^4$ or $R^5$, $R^6$, respectively, can be hydrogen;

$Y^1$, $Y^2$, $Y^3$, $Y^4$, $Y^5$, $Y^6$ are each, independently of one another, —O—, —OC(=)—, —C(=O)O—, —OC(=O)O— or a single bond;

$Z^1$ is —OC(=O)— or —C(=O)O—,

is phenylene-1,4-diyl, unsubstituted, monosubstituted, disubstituted or trisubstituted by F, pyrimidine-2,5-diyl, unsubstituted or monosubstituted by F, pyridine-2,5-diyl, unsubstituted or monosubstituted by F, pyridazine-2,5-diyl, unsubstituted or monosubstituted by F,

is phenylene-1,4-diyl, unsubstituted, monosubstituted, disubstituted or trisubstituted by F, pyrimidine-2,5-diyl, unsubstituted or monosubstituted by F, pyridine-2,5-diyl, unsubstituted or monosubstituted by F, pyridazine-2,5-diyl, unsubstituted or monosubstituted by F with the proviso that one of the rings A, B is one of the nitrogen heterocycles mentioned,

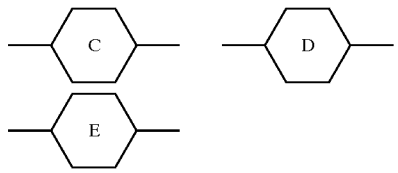

are each phenylene-1,4-diyl, independently of one another unsubstituted, mono substituted, disubstituted or trisubstituted by F with the proviso that at least one of the rings C, D, E is fluorophenylene-1,4-diyl or ortho-difluorophenylene-1,4-diyl,

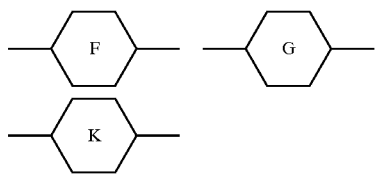

are each, independently of one another, phenylene-1,4-diyl, unsubstituted, monosubstituted, disubstituted or trisubstituted by F, pyrimidine-2,5-diyl, unsubstituted or monosubstituted by F, pyridine-2,5-diyl, unsubstituted or monosubstituted by F, pyridazine-2,5-diyl, unsubstituted or monosubstituted by F with the proviso that one of the rings F, G, K is one of the nitrogen heterocycles mentioned, $R^{20}$, $R^{21}$ are each, independently of one another,
a) hydrogen or an alkyl, alkenyl, alkyloxy or alkenyloxy radical having 2 to 12 carbon atoms, where one or two nonadjacent —CH$_2$— groups may be replaced by —OC(=O)—, —(O=)C—O—, —Si(CH$_3$)$_2$— or cyclopropane-1,2-diyl and one or more H atoms may be replaced by F or
b) a moiety having at least one asymmetric carbon atom which is either part of an alkyl group having 3 to 16 carbon atoms, where 1 to 4 nonadjacent —CH$_2$— groups may be replaced by —O—, —OC(=O)— or —(O=)C—O— and one of the substituents of the asymmetric carbon atom is —CH$_3$, —CF$_3$, —OCH$_3$, —CH$_3$, Cl, F, CN or —OCF$_3$, or part of a 3- to 7-membered heterocycle, where one or two nonadjacent —CH$_2$— groups may be replaced by —O— or one —CH$_2$— group may be replaced by —OC(=O)— or —(O=)C—O—, with the provisos that the moiety as defined in b) having at least one asymmetric carbon atom is present in at least one of $R^{20}$, $R^{21}$ and $M^{18}$ or $M^{19}$ is a single bond if the moiety having the asymmetric carbon atom is part of an alkyl chain, $A^{14}$, $A^{15}$, $A^{16}$, $A^{17}$ are each, independently of one another, 1,4-phenylene, unsubstituted, monosubstituted or disubstituted by F or Cl, 1,3-phenylene, unsubstituted, monosubstituted or disubstituted by F or Cl, cyclohexane-1,4-diyl, unsubstituted or monosubstituted by F or CN, cyclohex-1-ene-1,4-diyl, 1-5fluorocyclohex-1-ene-1,4-diyl, cyclohex-2-ene-1,4-diyl, 2-oxocyclohexane-1,4-diyl, 2-cyclohexen-1-one-3,6-diyl, 1-alkyl-1-sila-cyclohexane-1,4-diyl, bicyclo[2.2.2]octane-1,4-diyl, spiro[4.5]decane-2,8- diyl, spiro[5.5]undecane-3,9-diyl, indane-2,5-diyl, naphthalene-2,6-diyl, unsubstituted, monosubstituted or disubstituted by F or CN, pyrimidine-2,5-diyl, unsubstituted or monosubstituted by F, pyridine-2,5-diyl, unsubstituted or monosubstituted by F, pyrazine-2,5-diyl, unsubstituted or monosubstituted by F, pyridazine-3,6-diyl, quinoline-2,6-diyl, quinoline-3,7-diyl, isoquinoline-3,7-diyl, quinazoline-2,6-diyl, quinoxaline-2,6-diyl, 1,3-dioxane-2,5-diyl, thiophene-2,4-diyl, thiophene-2,5-diyl, 1,3-thiazole-2,4-diyl, 1,3-thiazole-2,5-diyl, isoxazole-3,5-diyl, benzthiazole-2,6-diyl, unsubstituted, monosubstituted or polysubstituted by F, benzthiazole-2,5-diyl, unsubstituted, monosubstituted or polysubstituted by F, 1,3,4-thiadiazole-2,5-diyl, piperidine-1,4-diyl or piperazine-1,4-diyl, $M^{14}$, $M^{15}$, $M^{16}$, $M^{17}$ are each, independently of one another, a single bond, —OC(=O)—, —(O=)C—O—, —OCH$_2$—, —CH$_2$—O—, —CH$_2$CH$_2$—, —(CH$_2$)$_4$— or —C=C—, $M^{18}$, $M^{19}$ are each, independently of one another, —OC(=O)—, —(O=)C—O—, —OCH$_2$—, —CH$_2$—O— or a single bond, a, b, c, d are each, independently of one another, zero or 1 with the proviso $1 \leq \{a+b+c+d\} \leq 3$ and the understanding that (—A$^x$—M$^x$—) is a single bond when the corresponding index is zero.

Component (D) is preferably present in an amount from 0 to 30% by weight, in particular from 0.05 to 20% by weight.

DETAILED DESCRIPTION OF THE INVENTION

Here and likewise hereinbelow, it will be understood that bivalent radicals were designated in the "free state". This designation is essential for the characterization of the compounds, although strictly in accordance with IUPAC rules, other designations of the bivalent radicals forming part of the entire Markush formula-meaning incorporation both as image and as mirror image would be possible.

In particular, the object is achieved according to the invention by using a chiral smectic liquid crystal mixture in which there is a monostable position of the director (longitudinal axis) and the deviation of this monostable position from the rubbing direction in the industrially relevant temperature range from 10 to 50° C. is less than 10 degrees, preferably less than 5 degrees, more preferably less than 4 degrees and particularly preferably less than 3 degrees.

The term "independently of one another" means that each of the stated radicals may be selected from the stated meanings independently of the selection of the other radicals. The radicals can thus be identical or different.

The advantageous phase sequence I—N*—Sc* (also termed I—N—C) in the context of the present invention applies even if a narrow SmA phase range exists between the N* phase and the Sc* phase, with said range not exceeding a temperature range of 2K.

Futhermore it may be advantageous for the LCD cell to have an asymmetrical structure, i.e. the top surface and the bottom surface of the cell differ in at least one feature apart form the active matrix itself. This is in particular the case:

when using unsymmetrical or unsymmetrically treated alignment layers (for example in the case of antiparallel rubbing)

when one of the two alignment layers is omitted when the step of rubbing one of the two alignment layers is omitted or changed when an unsymmetrical layer structure is introduced, for example by additional insulation layers having different properties on their top and bottom surfaces with all measures which finally result in exposure of the liquid crystal domain to an environment which is unsymmetrical in relation to a symmetry plane parallel to the electrode surfaces.

Expressly included is the advantageous use of the novel materials and mixtures for active matrix displays, antiferroelectric displays and smectic displays, the term "display" being intended to mean any type of optical display or switching device regardless of its size, structure, light guidance, addressing and use.

In particular, the term "active matrix display" as used herein includes an LCD in which one of the two substrates is replaced by the rear side of an IC chip (IC=integrated circuit) as described, for example, in D. M. Walba, Science 270, 250–251 (1995) or http://www.displaytech.com.

In particular, the object is achieved by a chiral smectic active matrix display comprising a liquid crystal layer in the form of a monostable liquid crystal domain having a tilt angle which is virtually constant over a broad temperature range.

The terms "domain" or "monodomain" as used herein mean a range of essentially constant director configuration which distinguishes the monostable display from the bistable conventional SSFLC display. While the SSFLC display features two stable director configurations which are optically very different, the active matrix display of the invention has only one domain whose director changes continuously with the voltage and returns to the same stable state when the voltage is switched off. The presence of a possible fine structure of this domain is irrelevant for the display of the invention provided that its elements have essentially the same optical properties as the domain itself and thus a high contrast can be achieved.

The processes for preparing the components of the liquid crystal mixtures of the active matrix displays according to the invention are known in principle, as is the preparation of liquid crystal mixtures from the individual components (see, for example, DE-A 198 57 352).

It has been found in accordance with the invention that active matrix displays in which the ferroelectric smectic phase is stable over a broad temperature range are obtainable by using the liquid crystal mixtures comprising at least one compound each from at least two of the substance classes (A), (B) and (C) and one or more compounds from substance class (D). Furthermore, the deviation of the monostable position from the rubbing direction is small in terms of magnitude and virtually constant over a broad temperature range. As a result, maximum contrast is achieved in the entire temperature range at a fixed polarizer position.

The minimum requirements for the mixture are thus at least one compound from the substance classes (A), (B), (D) or (A), (C), (D) or (B), (C), (D).

Preferred compounds of the individual substance classes are listed hereinbelow, the radicals being as defined above unless indicated otherwise.

Preferred compounds of the substance class (A) correspond to the formulae

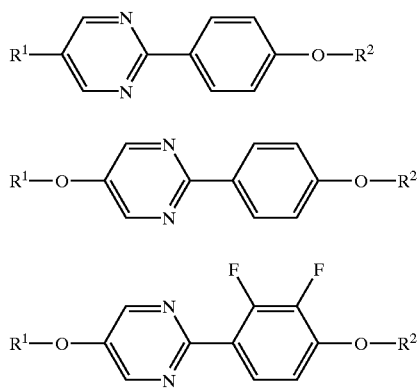

A1

A2

A3

Preferred compounds of the substance class (B) correspond to the formulae

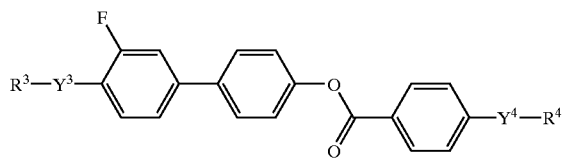

B1

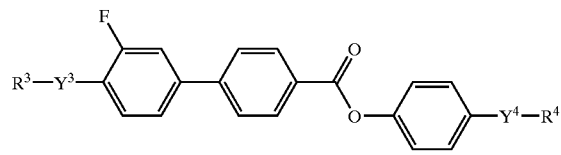

B2

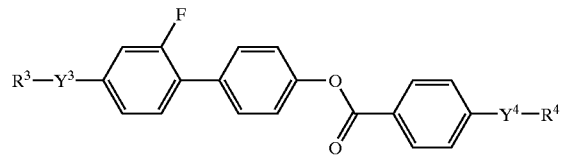

B3

B4

B5

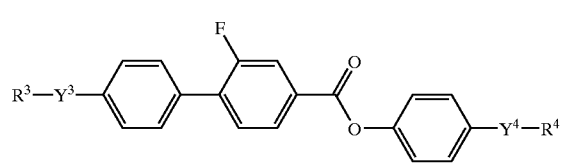

B6

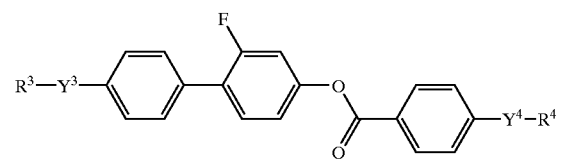

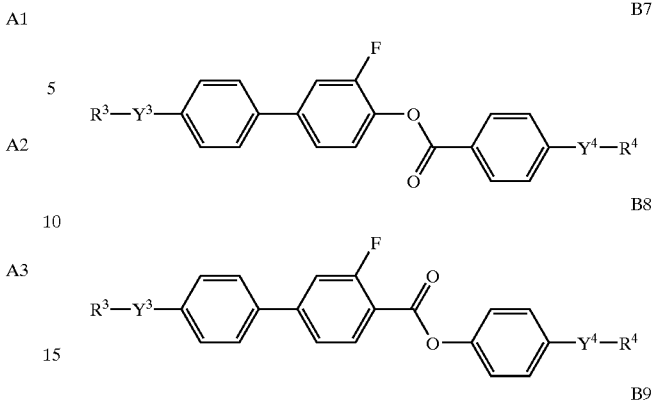

B7

B8

B9

B10 where $Y^3$ and $Y^4$ are each, independently of one another, a single bond or —O—.

Preferred compounds of the substance class (C) correspond to the formulae

C1

C2 where the ring F is pyrimidine-2,5-diyl or pyridine-2,5-diyl or 2-fluoropyridine-3,6-diyl, where the ring G is pyrimidine-2,5-diyl or pyridine-2,5-diyl or 2-fluoropyridine-3,6-diyl,

C3 where the ring K is pyrimidine-2,5-diyl or pyridine-2,5-diyl and $Y^5$ is in each case a single bond or —O—.

Preferred compounds of the substance class (D) are those in which said moiety having said at least one asymmetric carbon atom-which is termed R* here and hereinafter—in $R^{20}$ or $R^{21}$, respectively, contains at least one of the structural elements a) —C*H(F)—
b) —C*H(F)—C*H(F)—
c) —C*H(Cl)—
d) —C*H(CH$_3$)—
e) —C*H(CF$_3$)—
f) -oxirane-2,3-diylwhere $A^{14}$, $A^{15}$, $A^{16}$, $A^{17}$ are preferably each, independently of one another, phenylene-1,4-diyl, 2-fluorophenylene-1,4-diyl, 2,3-difluorophenylene-1,4-diyl, pyrimidine-2,5-diyl, pyridine-2,5-diyl, 2-fluoropyridine-3,6-diyl, cyclohexane-1,4-diyl, 1-cyanocyclohexane-1,4-diyl. It is also preferred that $A^{14}$ is cyclohexane-1,4-diyl when $R^{20}$ is hydrogen.

Particular preference is given to the compounds

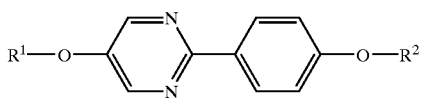

A2a in which the sum of the carbon atoms in $R^1$ and $R^2$ is from 14 to 22; in particular $R^1$ and $R^2$ contain at least 6 carbon atoms each;

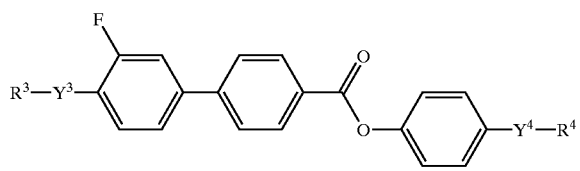

B2a in which $Y^3$ is —O—, $Y^4$ is a single bond and the sum of the carbon atoms in $R^3$ and $R^4$ is from 10 to 20, $R^3$ and $R^4$ preferably containing at least 4 carbon atoms each.

Particularly preferred compounds of the formulae C1, C2, C3 are those in which $R^5$ is an alkyl group having 4 to 10 carbon atoms and $R^6$ is an alkyl group having 5 to 12 carbon atoms.

Particularly preferred compounds of the substance class (D) are those in which one of $A^{14}$, $A^{15}$, $A^{16}$, $A^{17}$ is a pyrimidine-2,5-diyl or pyridine-2,5-diyl radical and R* is an alkyl group, where one —CH$_2$— group is replaced by —OC(=O)— or —C(—O)O—, at least one other (nonadjacent) —CH$_2$— group is replaced by —O— and the structural element —C*H(CH$_3$)— is present once or twice.

Other particularly preferred compounds of the substance class (D) are those in which one of $A^{14}$, $A^{15}$, $A^{16}$, $A^{17}$ is a pyrimidine-2,5-diyl or pyridine-2,5-diyl radical and R* is an alkyl group in which the structural element -oxirane-2,3-diyl- is present once.

The liquid crystal mixture of the display according to the invention particularly preferably comprises, in total, from 0.1 to 15% by weight of one or more compounds from substance class (D); most preferably the mixture comprises, in total, from 0.2 to 12% by weight of one or more compounds from substance class (D), based on the entire mixture. Preference is given to a mixture which has a spontaneous polarization in the operating temperature range of <20 nC/cm$^2$. Moreover, preference is given to a display wherein the liquid crystal mixture comprises at least two compounds of the formula A2a

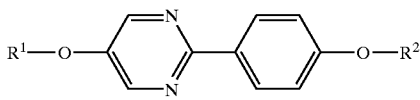

A2a in which the sum of the carbon atoms in $R^1$ and $R^2$ is from 14 to 22.

Furthermore, preference is given to a display wherein the liquid crystal mixture further comprises at least one compound from substance class (B), in which one of the rings C, D and E is fluorophenylene-1,4-diyl, $Y^3$, $Y^4$ are each, independently of one another, a single bond or —O— and the sum of the carbon atoms in $R^3$ and $R^4$ is from 10 to 20, and at least one compound from substance class (C), in which the nitrogen-containing ring is pyridine-2,5-diyl, $R^5$ is an alkyl group having 4 to 10 carbon atoms and $R^6$ is an alkyl group having 5 to 12 carbon atoms. The invention also relates to the liquid crystal mixtures described above.

The invention is explained in greater detail by the examples below. Percentages are by weight.

EXAMPLES

An LCD test cell is prepared from two commercially avalaible glass plates which are transparently and conductively coated with indium-tin oxide. The plates are spin-coated (2500 rpm, 10 s) with the alignment layer LQT-120 (from Hitachi Chemicals KK) which was diluted to 8.3% of its original solids content using N-methylpyrrolidone, cured by heating (230° C., 1 h) and then aligned by subjecting them to a rubbing process (rubbing material: rayon type YA-20-R*, clearance 0.2 mm, once, roller speed 700 rpm, substrate speed 10 cm/s, roller diameter 10 cm).

The rubbed glass plates are arranged such that the rubbing direction is antiparallel, adhesively bonded to produce test cells and set 1.3 μm apart by means of a spacer.

The FLC mixture is introduced into the cell and initially aligned in the nematic or cholesteric phase by cooling. On further cooling, a 3 V direct voltage is applied and the cell is transferred into the Sc* phase (chiral smectic C) range at a cooling rate of 2 K/min. During this process, a monostable monodomain is formed.

In the following inventive and comparative examples, the above-described alignment is carried out by applying the 3 V direct voltage in the temperature range of ±2 K at the N/Sc* phase transition point.

Example 1

A chiral smectic liquid crystal mixture consisting of

| | |
|---|---|
| 2-(4-hexyloxyphenyl)-5-octyloxy-pyrimidine | 5% |
| 2-(4-octyloxyphenyl)-5-octyloxy-pyrimidine | 2.5% |
| 2-(4-butyloxyphenyl)-5-octyloxy-pyrimidine | 4.9% |
| 2-(4-decyloxyphenyl)-5-octyloxy-pyrimidine | 4.9% |
| 2-(4-octyloxyphenyl)-5-octyl-pyrimidine | 7.5% |
| 2-(4-hexyloxyphenyl)-5-octyl-pyrimidine | 7.7% |
| 2-(4-decyloxyphenyl)-5-octyl-pyrimidine | 5.9% |
| 4-(5-dodecyl-pyrimidine-2-yl)phenyl trans-4-pentylcyclohexanecarboxylate | 6.5% |
| 2-(4-decyloxy-2,3-difluorophenyl)-5-nonyl-pyrimidine | 10% |
| 5-(octyloxycarbonyloxy)-2-(4-octyloxyphenyl)pyrimidine | 10% |
| 4-(5-undecyl-pyrimidine-2-yl)phenyl 5-butyl-thiophene-2-carboxylate | 16% |
| (S)-5-decyl-2-[4-(2-fluorodecyl)oxy-phenyl]pyrimidine | 4% |

| | |
|---|---|
| 4-[2-(4-hexylphenyl)-pyridmidine-5-yl]phenyl undecane-carboxylate | 15% | has the phase transition values I/N*=95.6–90.3° C. and N*/Sc*=79.3° C. and a tilt angle (at Tc-30° C.; 10 V/20 V) of 23.6/25.7°.

FIG. 1 depicts the profile of the voltage/transmission (Tr %) values at Tc-30° C. (in this case correspondingly at 49.3° C.) in accordance with the above measurement set-up.

Example 2

The mixture of Example 1, but comprising 15% of 2-(4-hexylphenyl)-5-(4-hexylphenyl)pyridine instead of 4-[2-(4-hexylphenyl)-pyrimidine-5-yl]phenyl undecanecarboxylate, has the phase transition values I/N*=93.7–91.4° C. and N*/Sc*=75.2° C. and a tilt angle (at Tc-30° C.; 10 V/20 V) of 22.2/25.9°.

Figure 2:
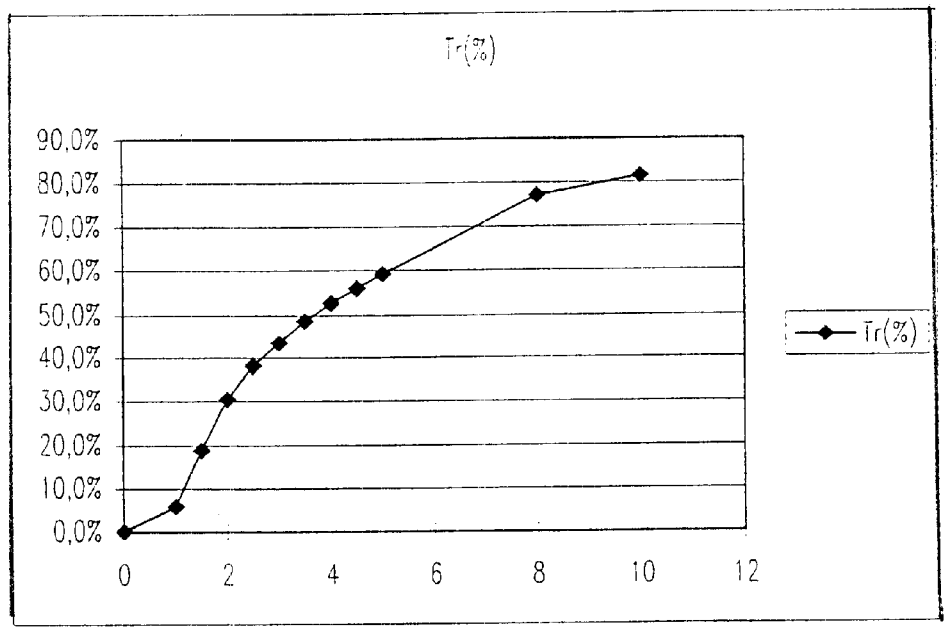

FIG. 2 depicts the profile of the voltage/transmission values at Tc-30° C. in accordance with the above measurement set-up.

Example 3

The mixture of Example 1, but comprising 15% of 2-(4'-propyl-biphenyl-4-yl)-5-octyl-pyrimidine instead of 4-[2-(4-hexylphenyl)-pyrimidine-5-yl]phenyl undecanecarboxylate, has the phase transition values I/N*=92.6–90.4° C. and N*/Sc*=66.7° C. and a tilt angle (at Tc-30° C.; 10 V/20 V) of 25.6/27.1°.

Figure 3:
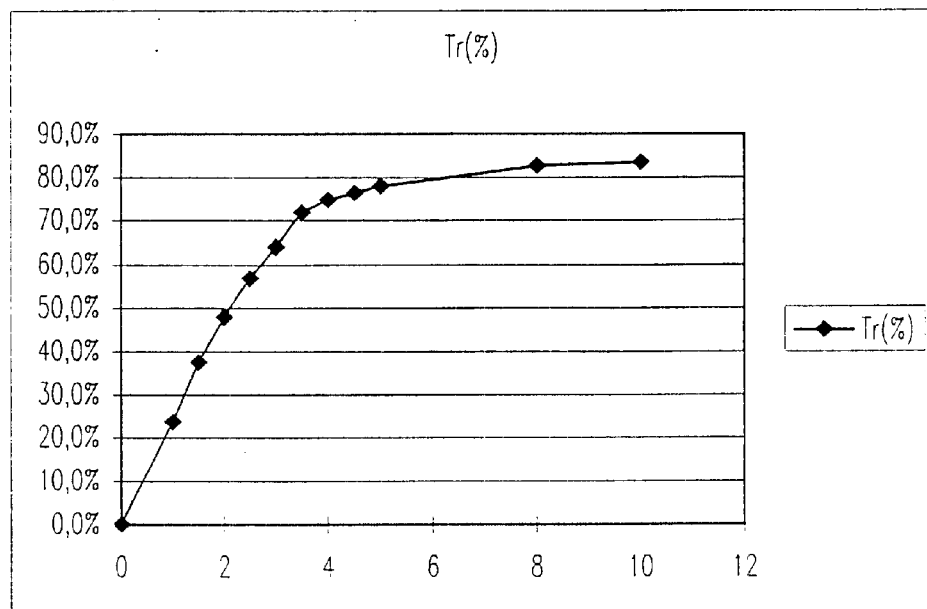

FIG. 3 depicts the profile of the voltage/transmission values at Tc-30° C. in accordance with the above measurement set-up.

Example 4

The mixture of Example 1, but comprising 15% of 2-fluoro-(4-pentylphenyl)-6-(4-nonylphenyl)pyridine instead of 4-[2-(4-hexylphenyl)-pyrimidine-5-yl]phenyl undecanecarboxylate, has the phase transition values I/N*=89.0–87.2° C. and N*/Sc*=67.4° C. and a tilt angle (at Tc-30° C.; 10 V/20 V) of 28/29.3°.

Figure 4:
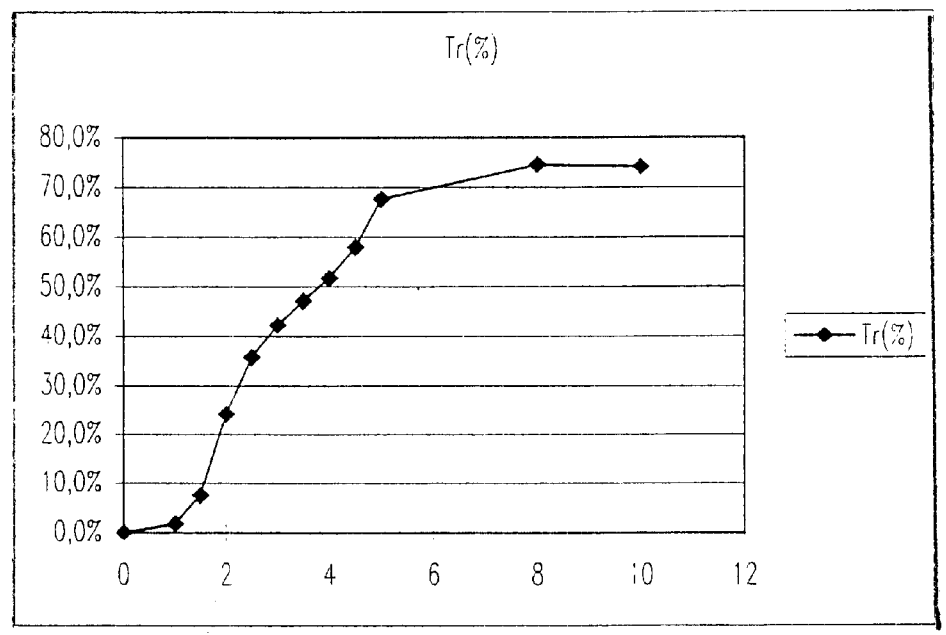

FIG. 4 depicts the profile of the voltage/transmission values at Tc-30° C. in accordance with the above measurement set-up.

Example 5

The mixture of Example 1, but comprising 15% of 2-fluoro-3-(4-hexylphenyl)-6-(4-octyloxyphenyl)pyridine instead of 4-[2-(4-hexylphenyl)-pyrimidine-5-yl]phenyl undecanecarboxylate, has the phase transition values I/N* 91.0–89.0° C. and N*/Sc*=69.7° C. and a tilt angle (at Tc-30° C.; 10 V/20 V) of 29.5/31°.

Figure 5:
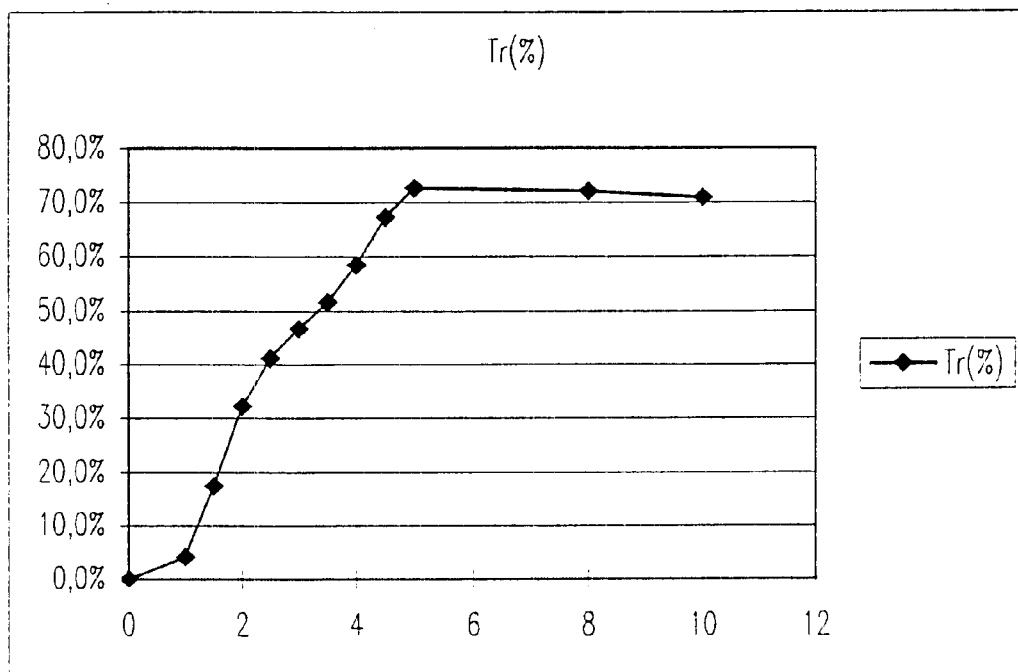

FIG. 5 depicts the profile of the voltage/transmission values at Tc-30° C. in accordance with the above measurement set-up.

Example 6

The mixture of Example 1, but comprising 15% of (2-fluoro-4-heptyl)phenyl 3'-fluoro-4'-octyloxy-biphenyl-4-carboxylate instead of 4-[2-(4-hexylphenyl)-pyrimidine-5-yl]phenyl undecanecarboxylate, has the phase transition values I/N*=88.1–86.6° C. and N*/Sc*=62.5° C. and a tilt angle (at Tc-30° C.; 10 V/20 V) of 29.9/31.1°.

Figure 6:
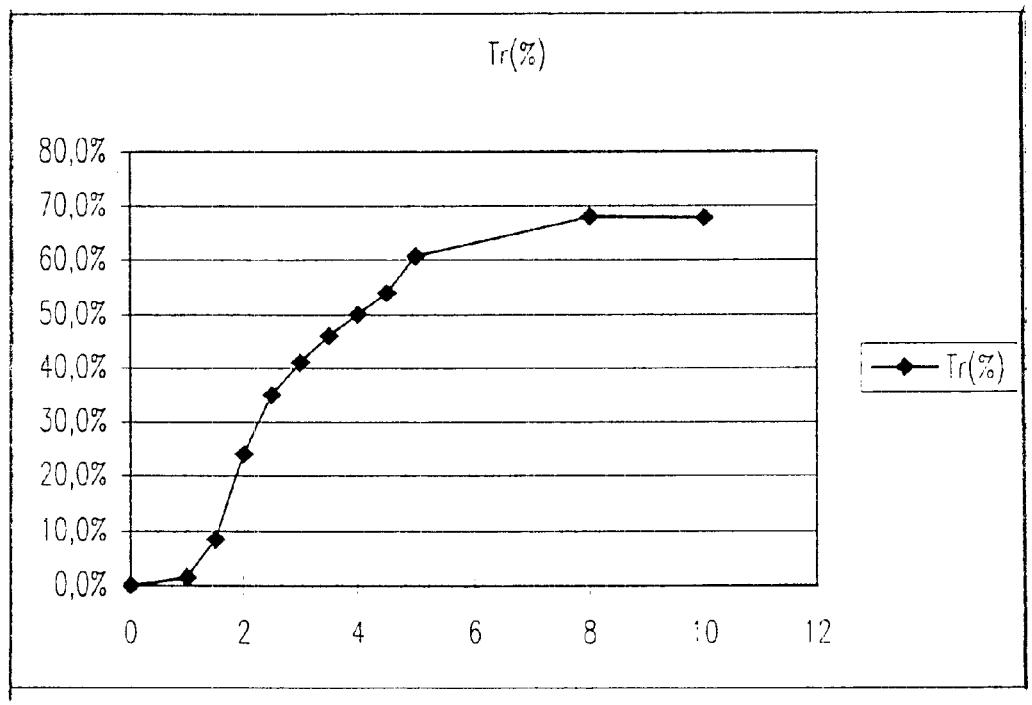

FIG. 6 depicts the profile of the voltage/transmission values at Tc-30° C. in accordance with the above measurement set-up.

Example 7

The mixture of Example 1, but comprising 15% of 2-fluoro-4-pentyl)phenyl 4'-heptyloxy-biphenyl-4-carboxylate instead of 4-[2-(4-hexylphenyl)-pyrimidine-5-yl]phenyl undecanecarboxylate, has the phase transition values I/N*=90.0–88.4° C. and N*/Sc*=62.9° C. and a tilt angle (at Tc-30° C.; 10 V/20 V) of 27.2/28.7°.

Figure 7:
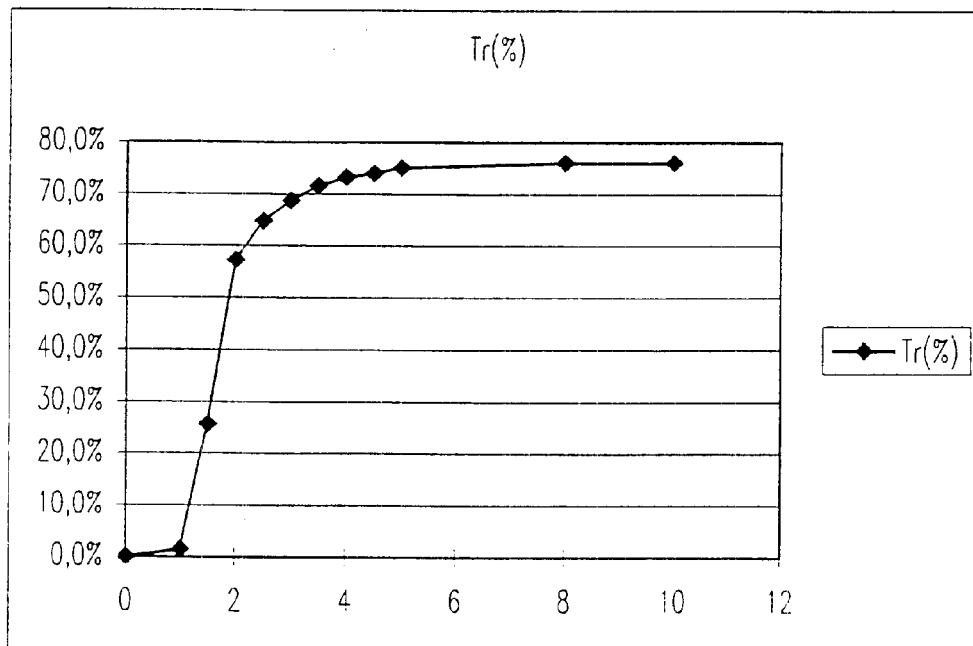

FIG. 7 depicts the profile of the voltage/transmission values at Tc-30° C. in accordance with the above measurement set-up.

Example 8

The mixture of Example 1, but comprising 15% of 2-fluoro-4-pentyl)phenyl 4'-octyloxy-biphenyl-4-carboxylate instead of 4-[2-(4-hexylphenyl)-pyrimidine-5-yl]phenyl undecanecarboxylate, has the phase transition values I/N*=89.2–87.2° C. and N*/Sc*=63.8° C. and a tilt angle (at Tc-30° C.; 10 V/20 V) of 27.4/28.6°.

FIG. 8 depicts the profile of the voltage/transmission values at Tc-30° C. in accordance with the above measurement set-up.

Example 9

The mixture of example 1, but comprising 7.5% of 2-fluoro-4-pentyl)phenyl 4'-octyloxy-biphenyl-4-carboxylate and 7.5% of 2-fluoro-3-(4-pentylphenyl)-6-(4-nonylphenyl)pyridine instead of 4-[2-(4-hexylphenyl)-pyrimidine-5-yl]phenyl undecanecarboxylate, has the phase transition values I/N*=89.0–87.0° C. and N*/Sc*=65.4° C. and a tilt angle (at Tc-30° C.; 10 V/20 V) of 27.6/28.8°.

Figure 9:
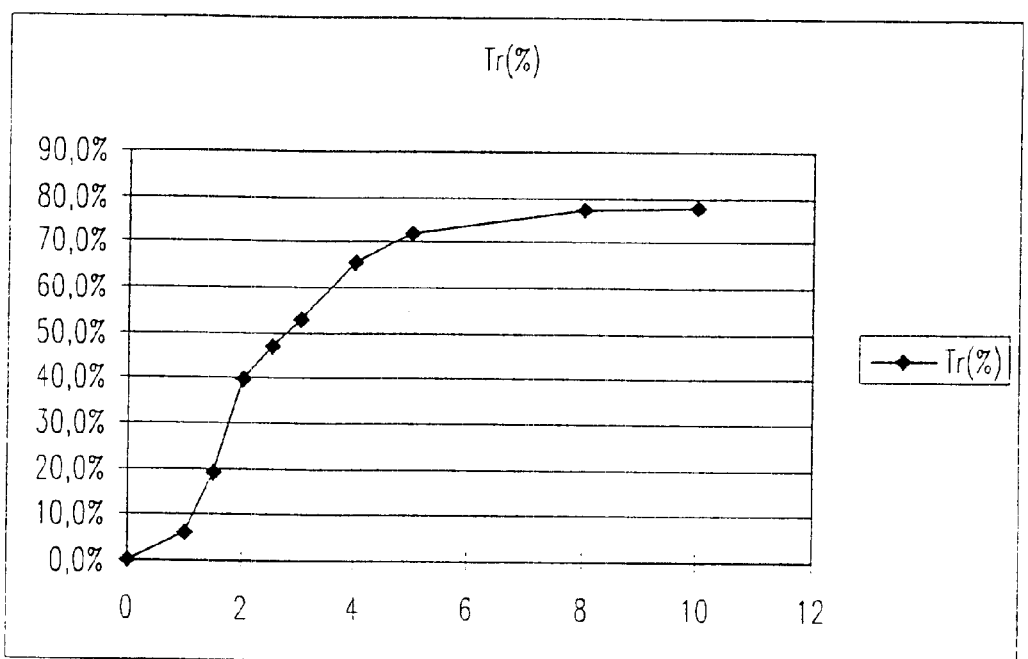

FIG. 9 depicts the profile of the voltage/transmission values at Tc-30° C. in accordance with the above measurement set-up.

What is claimed is:

1. An active matrix display comprising a chiral smectic liquid crystal mixture where the liquid crystal mixture is characterized by the phase sequence I—N*—SmC*, a spontaneous polarization in the operating temperature range of <40 nC/cm² and a pitch of >10 μm at at least one temperature in the nematic or cholesteric phase and comprises at least one compound each from at least two of the substance classes (A), (B) and (C) and from 0.1 to 50% by weight, based on the liquid crystal mixture, of one or more compounds from substance class (D)

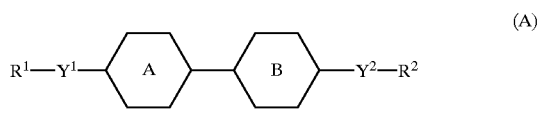

(A)

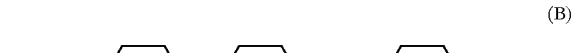

(B)

(C)

$$R^{20}-M^{18}-(-A^{14}-M^{14})_a(-A^{15}-M^{15})_b-(-M^{16}-A^{16})_c-(-M^{17}-A^{17})_d-M^{19}-R^{21} \quad \text{(D)}$$

where:

R$^1$, R$^2$, R$^3$, R$^4$, R$^5$, R$^6$ are each, independently of one another, hydrogen or a straight-chain or branched alkyl or alkenyl radical (with or without asymmetric carbon atoms) having 2 to 18 carbon atoms, where one or two nonterminal, nonadjacent —CH$_2$— groups may be replaced by —O— and/or one —CH$_2$— group may be replaced by —C≡C— or —Si(CH$_3$)$_2$— and one or more H atoms may be replaced by F with the provisos that heteroatoms cannot be adjacent and that in each case only one of R$^1$, R$^2$ or R$^3$, R$^4$ or R$^5$, R$^6$, respectively, can be hydrogen;

Y$^1$, Y$^2$, Y$^3$, Y$^4$, Y$^5$, Y$^6$ are each, independently of one another, —O—, —OC(=O)—, —C(=O)O—, —OC(=O)O— or a single bond;

Z$^1$ is —OC(=O)— or —C(=O)O—,

is phenylene-1,4-diyl, unsubstituted, monosubstituted, disubstituted or trisubstituted by F, pyrimidine-2,5-diyl, unsubstituted or monosubstituted by F, pyridine-2,5-diyl, unsubstituted or monosubstituted by F, pyridazine-2,5-diyl, unsubstituted or monosubstituted by F,

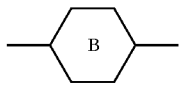

is phenylene-1,4-diyl, unsubstituted, monosubstituted, disubstituted or trisubstituted by F, pyrimidine-2,5-diyl, unsubstituted or monosubstituted by F, pyridine-2,5-diyl, unsubstituted or monosubstituted by F, pyridazine-2,5-diyl, unsubstituted or monosubstituted by F with the proviso that one of the rings A, B is one of the nitrogen heterocycles mentioned,

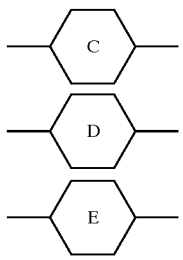

are each phenylene-1,4-diyl, independently of one another unsubstituted, monosubstituted, disubstituted or trisubstituted by F with the proviso that at least one of the rings C, D, E is fluorophenylene-1,4-diyl or

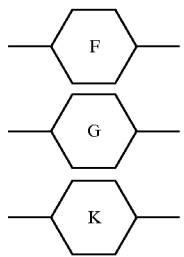

are each, independently of one another, phenylene-1,4-diyl, unsubstituted, monosubstituted, disubstituted or trisubstituted by F, pyrimidine-2,5-diyl, unsubstituted or monosubstituted by F, pyridine-2,5-diyl, unsubstituted or monosubstituted by F, pyridazine-2,5-diyl, unsubstituted or monosubstituted by F with the proviso that one of the rings F, G, K is one of the nitrogen heterocycles mentioned, R$^{20}$, R$^{21}$ are each, independently of one another, a) hydrogen or an alkyl, alkenyl, alkyloxy or alkenyloxy radical having 2 to 12 carbon atoms, where one or two nonadjacent —CH$_2$— groups may be replaced by —OC(=O)—, —(O=)C—O—, —Si(CH$_3$)$_2$— or cyclopropane-1,2-diyl and one or more H atoms may be replaced by F or b) a moiety having at least one asymmetric carbon atom which is either part of an alkyl group having 3 to 16 carbon atoms, where 1 to 4 nonadjacent —CH$_2$— groups may be replaced by —O—, —OC(=O)— or —(O=)C—O— and one of the substituents of the asymmetric carbon atom is —CH$_3$, —CF$_3$, —OCH$_3$, —CH$_3$, Cl, F, CN or —OCF$_3$, or part of a 3- to 7-membered heterocycle, where one or two nonadjacent —CH$_2$— groups may be replaced by —O— or one —CH$_2$— group may be replaced by —OC(=O)— or —(O=)C—O—, with the proviso that the moiety as defined in b) having at least one asymmetric carbon atom is present in at least one of R$^{20}$, R$^{21}$ and M$^{18}$ or M$^{19}$ is a single bond if the moiety having the asymmetric carbon atom is part of an alkyl chain, A$^{14}$, A$^{15}$, A$^{16}$, A$^{17}$ are each, independently of one another, 1,4-phenylene, unsubstituted, monosubstituted or disubstituted by F or Cl, 1,3-phenylene, unsubstituted, monosubstituted or disubstituted by F or Cl, cyclohexane-1,4-diyl, unsubstituted or monosubstituted by F or CN, cyclohex-1-ene-1,4-diyl, 1-fluorocyclohex-1-ene-1,4-diyl, cyclohex-2-ene-1,4-diyl, 2-oxocyclohexane-1,4-diyl, 2-cyclohexen-1-one-3,6-diyl, 1-alkyl-1-sila-cyclohexane-1,4-diyl, bicyclo[2.2.2]octane-1,4-diyl, spiro[4.5]decane-2,8-diyl, spiro[5.5]undecane-3,9-diyl, indane-2,5-diyl, naphthalene-2,6-diyl, unsubstituted, monosubstituted or disubstituted by F or CN, pyrimidine-2,5-diyl, unsubstituted or monosubstituted by F, pyridine-2,5-diyl, unsubstituted or monosubstituted by F, pyrazine-2,5-diyl, unsubstituted or monosubstituted by F, pyridazine-3,6-diyl, quinoline-2,6-diyl, quinoline-3,7-diyl, isoquinoline-3,7-diyl, quinazoline-2,6-diyl, quinoxaline-2,6-diyl, 1,3-dioxane-2,5-diyl, thiophene-2,4-diyl, thiophene-2,5-diyl, 1,3-thiazole-2,4-diyl, 1,3-thiazole-2,5-diyl, isoxazole-3,5-diyl, benzthiazole-2,6-diyl, unsubstituted, monosubstituted or polysubstituted by F, benz-thiazole-2,5-diyl, unsubstituted, monosubstituted or polysubstituted by F, 1,3,4-thiadiazole-2,5-diyl, piperidine-1,4-diyl or piperazine-1,4-diyl, $M^{14}$, $M^{15}$, $M^{16}$, $M^{17}$ are each, independently of one another, a single bond, —OC(=O)—, —(O=)C—O—, —OCH$_2$—, —CH$_2$—O—, —CH$_2$CH$_2$—, —(CH$_2$)$_4$— or —C≡C—, $M^{18}$, $M^{19}$ are each, independently of one another, —OC(=O)—, —(O=)C—O—, —OCH$_2$—, —CH$_2$—O— or a single bond, and a, b, c, d are each, independently of one another, zero or 1 with the proviso $1 \leq \{a+b+c+d\} \leq 3$.

2. An active matrix display as claimed in claim 1, wherein the liquid crystal mixture is present in the form of a monostable liquid crystal domain.

3. An active matrix display as claimed in claim 1, wherein the liquid crystal mixture comprises at least one compound from each of the substance classes (A) and (D) and at least one compound from at least one of the substance classes (B) and (C).

4. An active matrix display as claimed in claim 1, wherein the liquid crystal mixture comprises at least two compounds from substance class (A).

5. An active matrix display as claimed in claim 4, wherein the liquid crystal mixture comprises at least two compounds of the formula A2a

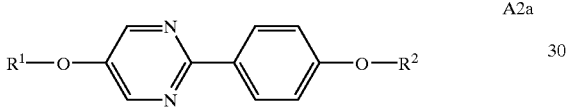

A2a in which the sum of the carbon atoms in $R^1$ and $R^2$ is from 14 to 22.

6. An active matrix display as claimed in claim 5, wherein the liquid crystal mixture comprises at least one compound from substance class (B), in which one of the rings C, D and E is fluorophenylene-1,4-diyl, $Y^3$ and $Y^4$ are each, independently of one another, a single bond or —O— and the sum of the carbon atoms in $R^3$ and $R^4$ is from 10 to 20, and at least one compound from substance class (C), in which the nitrogen-containing ring is pyridine-2,5-diyl, $R^5$ is an alkyl group having 4 to 10 carbon atoms and $R^6$ is an alkyl group having 5 to 12 carbon atoms.

7. A liquid crystal mixture comprising a chiral smectic liquid crystal mixture where the liquid crystal mixture is characterized by the phase sequence I—N*—SmC*, a spontaneous polarization in the operating temperature range of <40 nC/cm$^2$ and a pitch of >10 μm at at least one temperature in the nematic or cholesteric phase and comprises at least one compound each from at least two of the substance classes (A), (B) and (C) and from 0.1 to 50% by weight, based on the liquid crystal mixture, of one or more compounds from substance class (D)

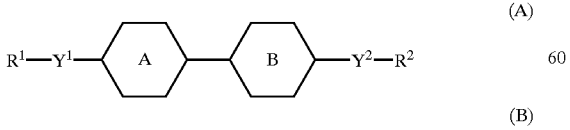

(A)

(B)

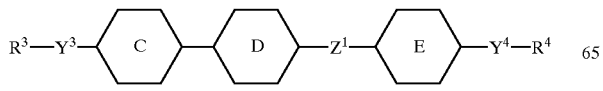

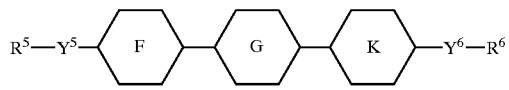

(C)

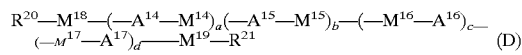

(D)

where:

$R^1$, $R^2$, $R^3$, $R^4$, $R^5$, $R^6$ are each, independently of one another, hydrogen or a straight-chain or branched alkyl or alkenyl radical (with or without asymmetric carbon atoms) having 2 to 18 carbon atoms, where one or two nonterminal, nonadjacent —CH$_2$— groups may be replaced by —O— and/or one —CH$_2$— group may be replaced by —C≡C— or —Si(CH$_3$)$_2$— and one or more H atoms may be replaced by F with the provisos that heteroatoms cannot be adjacent and that in each case only one of $R^1$, $R^2$ or $R^3$, $R^4$ or $R^5$, $R^6$, respectively, can be hydrogen;

$Y^1$, $Y^2$, $Y^3$, $Y^4$, $Y^5$, $Y^6$ are each, independently of one another, —O—, —OC(=O)—, —C(=O)O—, —OC(=O)O— or a single bond;

$Z^1$ is —OC(=O)— or —C(=O)O—,

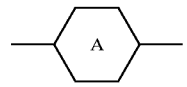

is phenylene-1,4-diyl, unsubstituted, monosubstituted, disubstituted or trisubstituted by F, pyrimidine-2,5-diyl, unsubstituted or monosubstituted by F, pyridine-2,5-diyl, unsubstituted or monosubstituted by F, pyridazine-2,5-diyl, unsubstituted or monosubstituted by F,

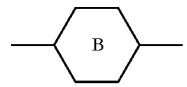

is phenylene-1,4-diyl, unsubstituted, monosubstituted, disubstituted or trisubstituted by F, pyrimidine-2,5-diyl, unsubstituted or monosubstituted by F, pyridine-2,5-diyl, unsubstituted or monosubstituted by F, pyridazine-2,5-diyl, unsubstituted or monosubstituted by F with the proviso that one of the rings A, B is one of the nitrogen heterocycles mentioned,

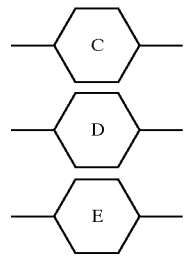

are each phenylene-1,4-diyl, independently of one another unsubstituted, monosubstituted, disubstituted or trisubstituted by F with the proviso that at least one of the rings C, D, E is fluorophenylene-1,4-diyl or ortho-difluorophenylene-1,4-diyl,

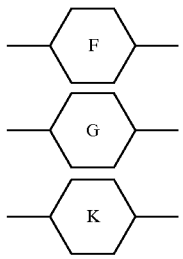

are each, independently of one another, phenylene-1,4-diyl, unsubstituted, monosubstituted, disubstituted or trisubstituted by F, pyrimidine-2,5-diyl, unsubstituted or monosubstituted by F, pyridine-2,5-diyl, unsubstituted or monosubstituted by F, pyridazine-5-diyl, unsubstituted or monosubstituted by F with the proviso that at least one of the rings F, G, K is one of the nitrogen heterocycles mentioned, $R^{20}$, $R^{21}$ are each, independently of one another, c) hydrogen or an alkyl, alkenyl, alkyloxy or alkenyloxy radical having 2 to 12 carbon atoms, where one or two nonadjacent —$CH_2$— groups may be replaced by —OC(=O)—, —(O=)C—O—, —Si($CH_3$)$_2$— or cyclopropane-1,2-diyl and one or more H atoms may be replaced by F or d) a moiety having at least one asymmetric carbon atom which is either part of an alkyl group having 3 to 16 carbon atoms, where 1 to 4 nonadjacent —$CH_2$— groups may be replaced by —O—, —OC(=O)— or —(O=)C—O— and one of the substituents of the asymmetric carbon atom is —$CH_3$, —$CF_3$, —$OCH_3$, —$CH_3$, Cl, F, CN or —$OCF_3$, or part of a 3- to 7-membered heterocycle, where one or two nonadjacent —$CH_2$— groups may be replaced by —O— or one —$CH_2$— group may be replaced by —OC(=O)— or —(O=)C—O—, with the proviso that the moiety as defined in b) having at least one asymmetric carbon atom is present in at least one of $R^{20}$, $R^{21}$ and $M^{18}$ or $M^{19}$ is a single bond if the moiety having the asymmetric carbon atom is part of an alkyl chain, $A^{14}$, $A^{15}$, $A^{16}$, $A^{17}$ are each, independently of one another, 1,4-phenylene, unsubstituted, monosubstituted or disubstituted by F or Cl, 1,3-phenylene, unsubstituted, monosubstituted or disubstituted by F or Cl, cyclohexane-1,4-diyl, unsubstituted or monosubstituted by F or CN, cyclohex-1-ene-1,4-diyl, 1-fluorocyclohex-1-ene-1,4-diyl, cyclohex-2-ene-1,4-diyl, 2-oxocyclohexane-1,4-diyl, 2-cyclohexen-1-one-3,6-diyl, 1-alkyl-1-sila-cyclohexane-1,4-diyl, bicyclo[2.2.2]octane-1,4-diyl, spiro[4.5]decane-2,8-diyl, spiro[5.5]undecane-3,9-diyl, indane-2,5-diyl, naphthalene-2,6-diyl, unsubstituted, monosubstituted or disubstituted by F or CN, pyrimidine-2,5-diyl, unsubstituted or monosubstituted by F, pyridine-2,5-diyl, unsubstituted or monosubstituted by F, pyrazine-2,5-diyl, unsubstituted or monosubstituted by F, pyridazine-3,6-diyl, quinoline-2,6-diyl, quinoline-3,7-diyl, isoquinoline-3,7-diyl, quinazoline-2,6-diyl, quinoxaline-2,6-diyl, 1,3-dioxane-2,5-diyl, thiophene-2,4-diyl, thiophene-2,5-diyl, 1,3-thiazole-2,4-diyl, 1,3-thiazole-2,5-diyl, isoxazole-3,5-diyl, benzthiazole-2,6-diyl, unsubstituted, monosubstituted or polysubstituted by F, benz-thiazole-2,5-diyl, unsubstituted, monosubstituted or polysubstituted by F, 1,3,4-thiadiazole-2,5-diyl, piperidine-1,4-diyl or piperazine-1,4-diyl, $M^{14}$, $M^{15}$, $M^{16}$, $M^{17}$ are each, independently of one another, a single bond, —OC(=O)—, —(O=)C—O—, —$OCH_2$—, —$CH_2$—O—, —$CH_2CH_2$—, —$(CH_2)_4$— or —C≡C—, $M^{18}$, $M^{19}$ are each, independently of one another, —OC(=O)—, —(O=)C—O—, —$OCH_2$—, —$CH_2$—O— or a single bond, and a, b, c, d are each, independently of one another, zero or 1 with the proviso $1 \leq \{a+b+c+d\} \leq 3$.

* * * * *